(12) United States Patent
Zobele

(10) Patent No.: US 7,519,279 B2
(45) Date of Patent: Apr. 14, 2009

(54) PLUG AND HEATING ELEMENT ASSEMBLY FOR A DIFFUSING DEVICE FOR VOLATILE SUBSTANCES

(75) Inventor: Franco Zobele, Trento (IT)

(73) Assignee: Zobele Holding SpA, Trento (IT)

( * ) Notice: Subject to any disclaimer, the term of this patent is extended or adjusted under 35 U.S.C. 154(b) by 174 days.

(21) Appl. No.: 11/399,792

(22) Filed: Apr. 6, 2006

(65) Prior Publication Data
US 2006/0231544 A1  Oct. 19, 2006

(30) Foreign Application Priority Data
Apr. 19, 2005 (EP) ................. 05425244

(51) Int. Cl.
*F24F 3/14* (2006.01)
*F24F 6/00* (2006.01)
(52) U.S. Cl. .............................. 392/390; 392/392
(58) Field of Classification Search .......... 392/386–395; 239/44–50; 122/366, 367–1
See application file for complete search history.

(56) References Cited

U.S. PATENT DOCUMENTS

| | | | |
|---|---|---|---|
| 5,038,394 A * | 8/1991 | Hasegawa et al. | 392/395 |
| 5,095,647 A * | 3/1992 | Zobele et al. | 43/125 |
| 6,850,697 B2 * | 2/2005 | Basaganas Millan | 392/390 |
| 6,859,615 B2 * | 2/2005 | Yip et al. | 392/395 |
| 2004/0005146 A1 | 1/2004 | Wefler | 392/392 |

FOREIGN PATENT DOCUMENTS

| | | |
|---|---|---|
| EP | 0 716 807 A1 | 6/1996 |
| EP | 0 945 062 A1 | 9/1999 |
| EP | 1 302 106 A2 | 4/2003 |

\* cited by examiner

*Primary Examiner*—Sang Y Paik
(74) *Attorney, Agent, or Firm*—Merchant & Gould P.C.; Alan G. Gorman

(57) ABSTRACT

An assembly comprising a plug and a heating element. The plug comprises a body in which conducting poles are mounted for connection to an electrical socket, and the heating resistance comprises a body in which at least one electrical heating element, connected by means of electrical wires to the poles of the plug, the body of the heating element having a housing to receive a wick impregnated with volatile substances. At least one bridge connects the body of the plug to the body of the heating element, so as to avoid relative translation of the body of the plug with respect to the body of the heating element. The bridge has a breakable weakened part.

8 Claims, 4 Drawing Sheets

PLUG AND HEATING ELEMENT ASSEMBLY FOR A DIFFUSING DEVICE FOR VOLATILE SUBSTANCES

The present invention refers to a plug and heating element assembly for a diffusing device for volatile substances.

A diffusing device of the heating type generally comprises a heating element consisting of a plastic or ceramic support in which electrical resistances which heat up when passed through by an electrical current are inserted.

The heating element is coupled to a wick immersed in a solution to be diffused, contained in a containing shell, or to a tablet impregnated with the solution to be diffused. The electrical resistances of the heating element are connected by means of electrical wires to the poles of an electrical plug able to engage in an electrical socket connected to the supply main. To complete the assembly of the diffusing apparatus, the body of the electrical plug must be coupled with the body of the containing shell which must enclose the heating element.

Thus the heating element and the plug are connected to each other only by electrical wires. Since said electrical wires are flexible, the heating element has a great freedom of movement with respect to the plug. As a result, the mechanical coupling between the plug and the container shell proves somewhat complex and laborious.

In fact, we must consider that the heating element has three degrees of freedom with respect to the plug and can therefore move in any direction during the handling and the transport of the plug and heating element assembly. As a result, it is difficult to use robotized machines to assemble the plug to the containing shell, since these robots do not know the relative position of the heating element with respect to the plug.

Object of the present invention is to eliminate the drawbacks of the prior art by providing a plug and heating element assembly for a volatile substance diffusing device that is simple to assemble, also with the use of robotised machines.

Another object of the present invention is to provide a plug and heating element assembly for a diffusing device that is economical and not bulky and that does not require an excessive use of additional parts or elements.

Advantageous embodiments of the invention are apparent from the dependent claims.

The plug and heating element assembly for a volatile substance diffusing device comprises:
 a plug comprising a body in which conducting poles for the connection to an electrical socket are mounted, and
 a heating element comprising a body in which at least one electrical heating resistance, connected by means of electrical wires to the poles of the plug, is disposed.

The heating element is designed to be disposed near to or in contact with a tablet or a wick impregnated with volatile substances to promote diffusion of said volatile substances.

According to the invention at least a bridge connecting said body of the plug to said body of the heating element is provided, so as to avoid a relative translation of the plug body with respect to the heating element body.

In this manner the plug and heating element assembly can easily be mounted in the outer shell of the diffusing device, without problems of relative movements of the heating element with respect to the plug.

Further characteristics of the invention will be made clearer by the detailed description that follows, referring to purely exemplifying and therefore non-limiting embodiments thereof, illustrated in the appended drawings, in which.

Figure 1:
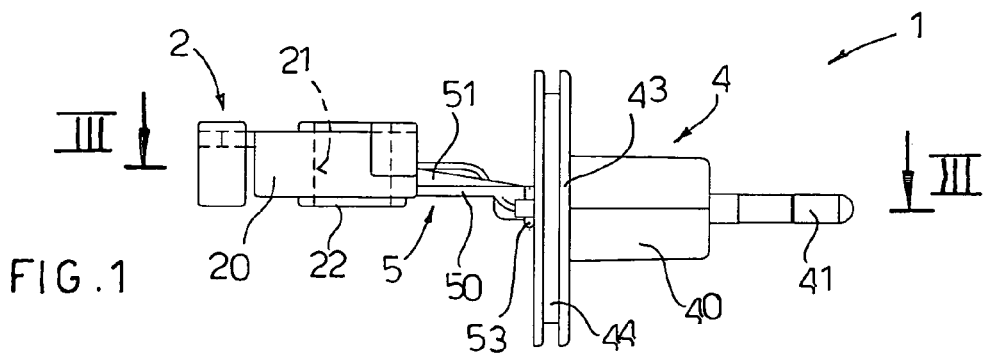
FIG. 1 is a side view showing a first embodiment of a plug and heating element assembly for a diffusing device for volatile substances according to the invention.
Figure 2:
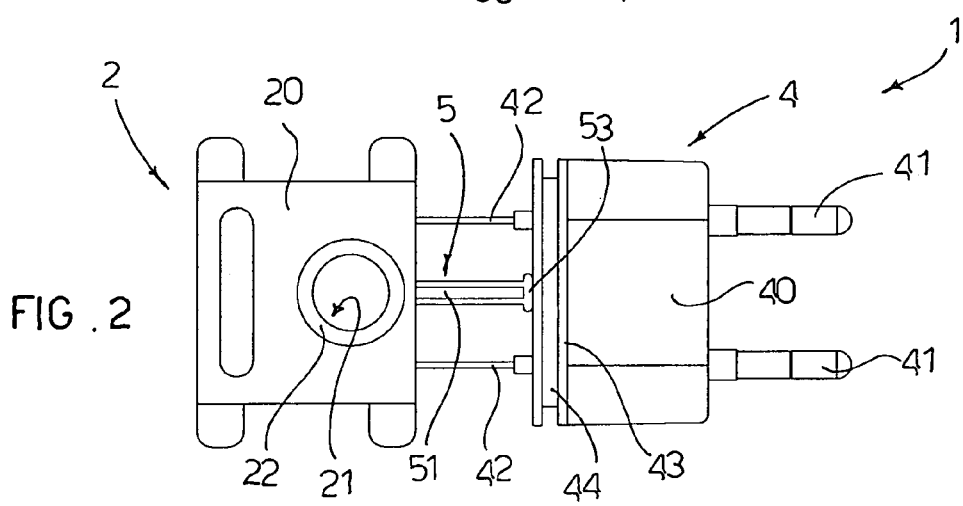
FIG. 2 is a top plan view of the plug and heating element assembly of FIG. 1.

A first embodiment of a plug and heating element assembly for a volatile substance diffusing device according to the invention is described with reference to FIGS. 1-4.

This assembly is indicated as a whole with the reference numeral 1 and comprises a heating element 2 and a plug 4.

The heating element 2 comprises a support or body 20 which can be made of plastic, of ceramic material or of any other electrically insulating material with characteristics of heat resistance and heat conduction. The support 20 is shown in a parallelepiped shape but it can also have a cylindrical or another shape.

The support 20 of the heating element 2 comprises a cylindrical tang 22 which defines a circular hole 21. A cylindrical wick (not shown) that is immersed in a volatile solution contained in a containing shell (not shown) is inserted in the hole 21 of the heating element 2.

Even if specific reference has been made to a wick, it is obvious that the heating element can have a seat to receive a tablet impregnated with the substance to be diffused and in any case the heating element is destined to be positioned near to or in contact with a support impregnated with the substance to be diffused.

Seats are formed in the support 20 of the heating element to accommodate electrical resistances 23 which heat up when passed through by an electrical current. The electrical resistances 23 are disposed tightly close to the tang 22 so as to heat it through heat conduction. In turn, the tang 22 of the heating element heats the wick through heat conduction. As a result, the heating of the wick promotes the diffusion of the volatile substances contained therein.

Two resistances 23 disposed in diametrically opposite positions with respect to the hole 21 and connected in series to each other have been shown in the figures; however, it is obvious that a single resistance or more than two resistances can be disposed in the support 20.

The resistances 23 can be locked in position by cementing into the support 20, or by using other sealing materials.

The plug 4 comprises a body 40 generally of insulating plastic which has housings in which conducting poles 41 are disposed. By way of example, two cylindrical poles are shown in the figures; however, it is obvious that according to the standards in force in the different countries, the plug 4 can also have flat poles or three poles.

The poles 41 of the plug 4 are connected by means of electrical cables 42 to the respective resistances 23. The wire strands of the electrical cables 42 are covered with an insulating sheath.

The body 40 of the plug has at its rear end a circular flange 43, disposed along a plane at right angles to the axis of the poles 41. Along the perimeter of the circular flange 43 a groove 44 is formed.

The plug 4 is able to couple rotatably with the outer shell of the diffusing device. For this purpose the outer shell has a circular hole defined by a circular frame that engages rotatably in the groove 44 of the flange 43 of the plug. In this manner the outer shell can be rotated with respect to the plug, so that the wick is always oriented in a vertical position, regardless of the orientation of the socket that receives the plug, to avoid possible leakage of the solution from the container shell.

Figure 3:
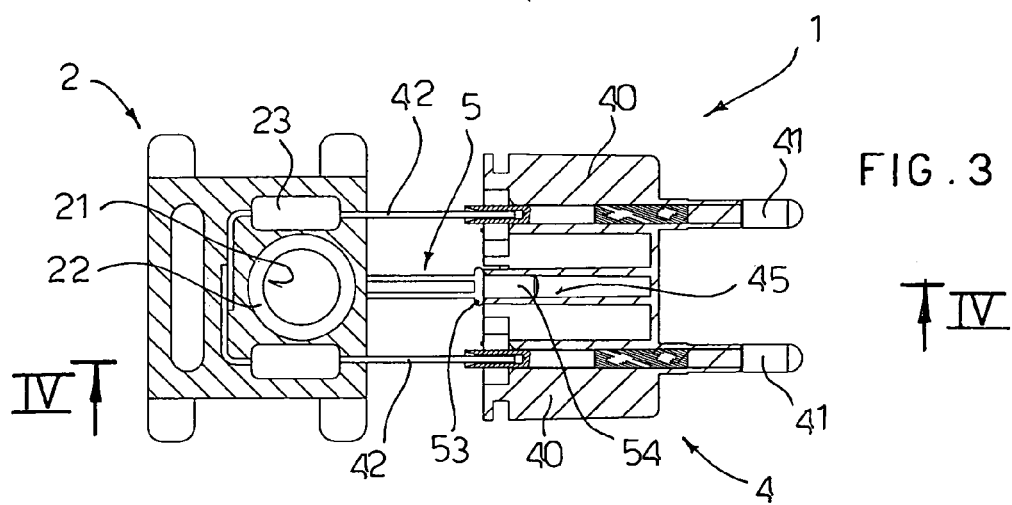
FIG. 3 is a sectional view taken along the line of section III-III of FIG. 1.
Figure 4:
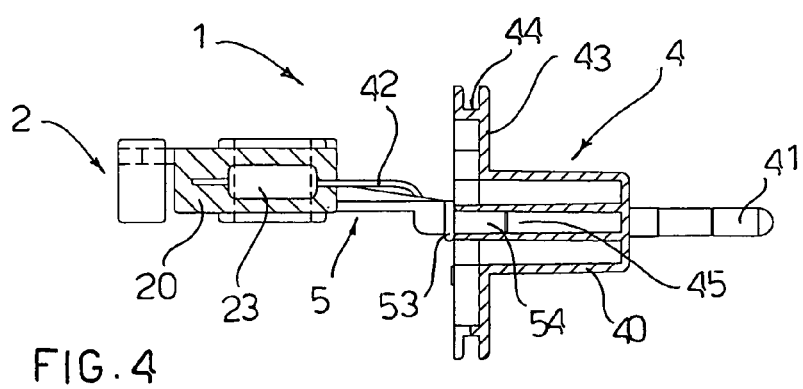
FIG. 4 is a sectional view taken along the line of section IV-IV of FIG. 3.

According to the invention, a bridge 5 is connected to the front edge of the support 20 of the heating element 2 and protrudes forward therefrom. The bridge 5 can take the form of a straight rod 50 with a reinforcing rib 51. The bridge 5 has at its free end an abutment flange 53 from which a cylindrical pin 54 protrudes forward (FIGS. 3 and 4).

The bridge 5 can be made in a single piece with the support 20 of the heating element, for example by injection moulding. Alternatively, the bridge 5 can be made integral with the support 20 of the heating element in any other manner, such as by welding, by gluing, by forced coupling and the like.

A cylindrical seat 45 (FIGS. 3 and 4), designed to receive in a rotating coupling relationship the cylindrical pin 54 of the bridge 5, is formed in the rear wall of the body 40. Thus the cylindrical pin 54 of the bridge is inserted in the cylindrical seat 45, until the abutment flange 53 of the bridge abuts against the rear wall of the plug 4 around the cylindrical seat 45.

In this manner the heating element 2 and the plug 4 are constrained to each other with two degrees of freedom. That is to say, the heating element 2 can rotate only with respect to the plug 4, around the axis of the pin 54. Thus any translating movement of the heating element 2 with respect to the plug 4 is prevented by the coupling of the pin 54 of the bridge inside the cylindrical seat 45 of the plug.

Thus the assembly of the diffusing device is simplified, thanks to the fixed position of the heating element with respect to the plug. In fact the outer shell can easily be coupled with the plug 4 and the heating element 2. Moreover, it must be considered that it is possible to have a rotating coupling between the plug and the outer shell and a fixed coupling between the heating element and the outer shell, precisely because the heating element is coupled rotatably with respect to the plug.

Hereunder like or corresponding elements to those already described are indicated with the same reference numerals and detailed description thereof will be omitted.

Figure 5:
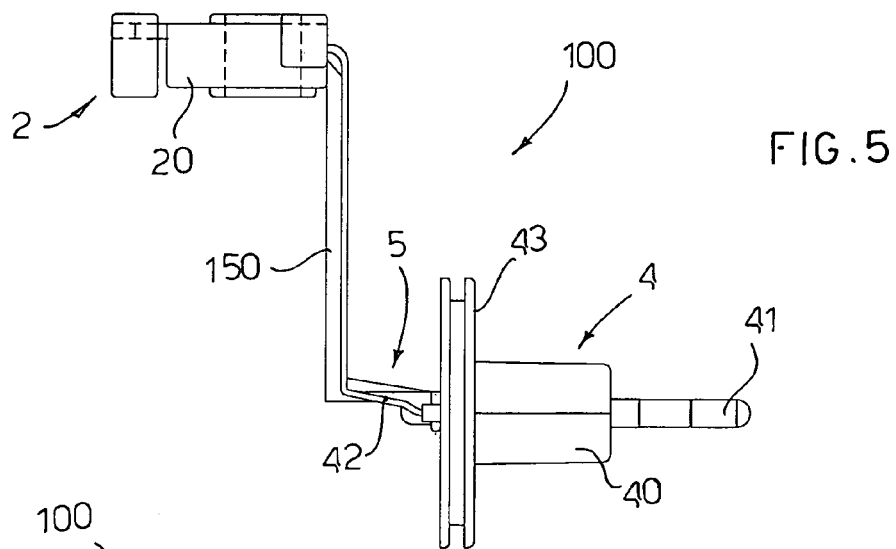
FIG. 5 is a side view showing a second embodiment of a plug and heating element assembly according to the invention.
Figure 6:
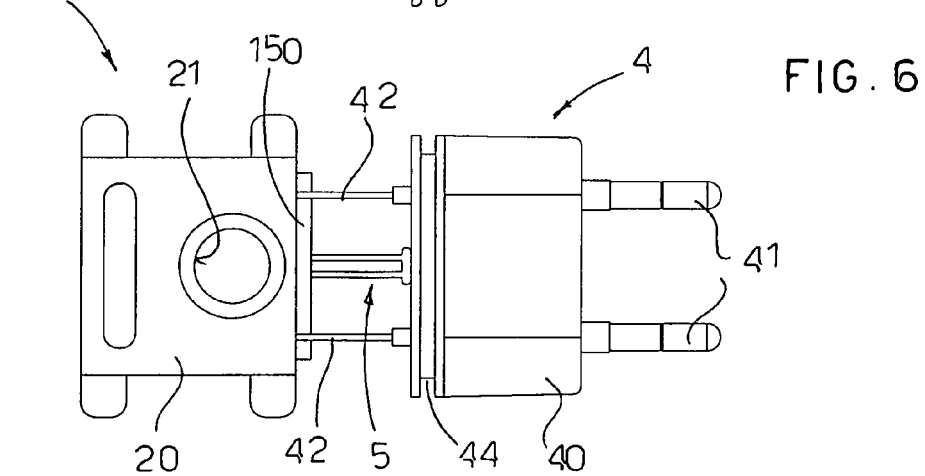
FIG. 6 is a top plan view of the plug and heating element assembly of FIG. 5.
Figure 7:
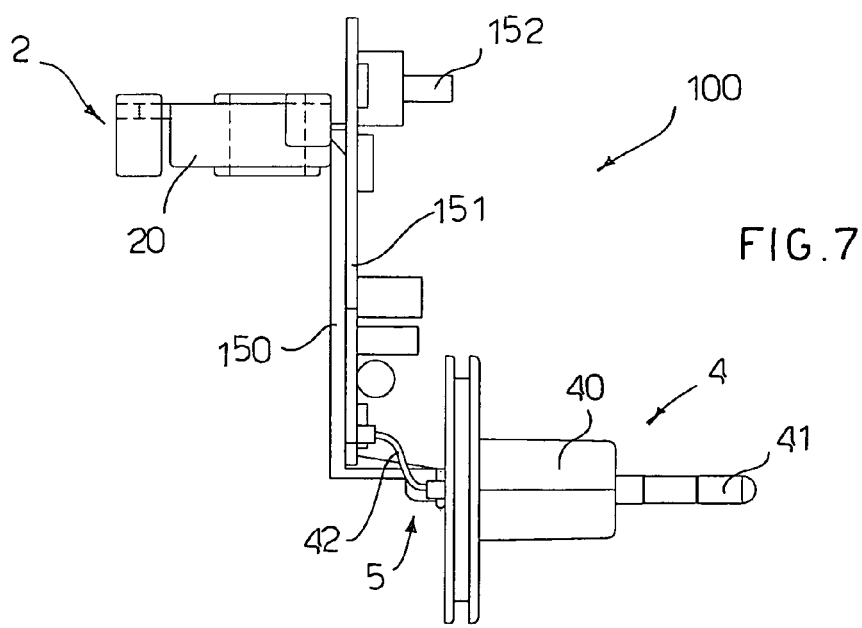
FIG. 7 is a side view showing the plug and heating element assembly of FIG. 6 in which a printed circuit board implementing some additional functions has been mounted.

A plug and heating element assembly according to a second embodiment of the invention, denoted as a whole with reference numeral 100, is described in FIGS. 5-7.

The heating element 2 and the plug 4 of the assembly 100 are substantially the same as those of the assembly 1 of the first embodiment. A bridge 5, substantially the same as that of the first embodiment, is coupled rotatably to the plug 4. A rectangular plate 150 which extends upward on a plane at right angles to the plane of the poles 41 of the plug is connected to the bridge 5. The top end of the plate 150 is fixed to the front surface of the body 20 of the heating element.

The plate 150 can be made of plastic material and coupled to the bridge 5 fixedly or rotatably.

A printed circuit board 151, on which is mounted a switch 152 that can be operated by the user, is fixed on the plate 150. Other optional devices, such as light devices (LED, lamps) and/or timers can be mounted on the circuit board 151.

Figure 8:
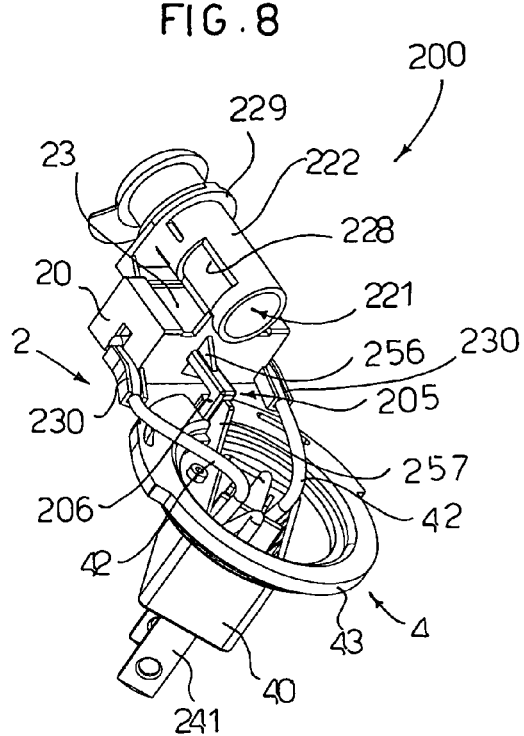
FIG. 8 is a partially broken off perspective view, showing a third embodiment of a plug and heating element assembly according to the invention.
Figure 9:
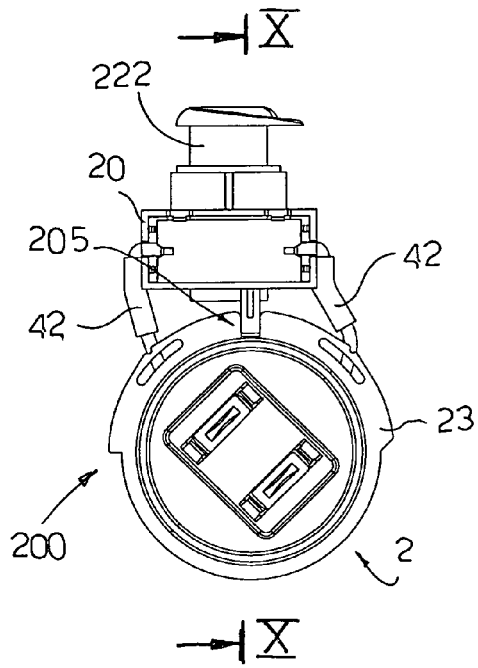
FIG. 9 is a top plan view of the plug and heating element assembly of FIG. 8.
Figure 10:
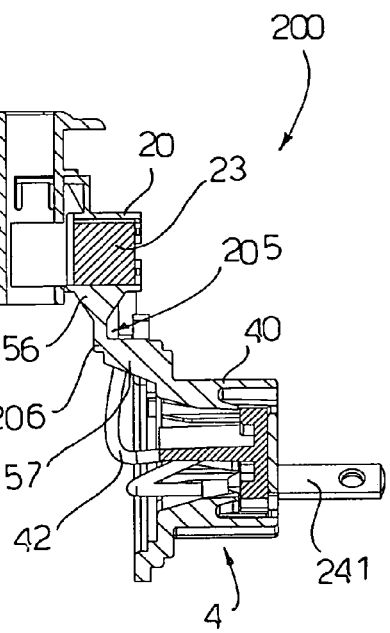
FIG. 10 is a sectional view taken along the plane of section X-X of FIG. 9.

A plug and heating element assembly according to a third embodiment of the invention, indicated as a whole with reference numeral 200, is illustrated in FIGS. 8-10.

In this case the poles 241 of the plug 4 are flat in accordance with United States standards. The heating element 2 comprises a parallelepiped body 20 inside which the electrical resistances 23 are disposed. Two seats 230, substantially U-shaped in cross-section, able to receive and to guide the electrical wires 42 from the poles 241 to the resistances 23, protrude from the body 20.

The body 20 has a circular connection 229 in which a cylindrical tang 222 defining a hole 221 to receive the wick is mounted rotatably. The tang 222 acts as a heat regulating element and for this purpose it has a slot 228 for the passage of the heat from the resistances 23 to the wick. In this manner, the flow of heat toward the wick is regulated by rotating the tang 22.

Figure 11:
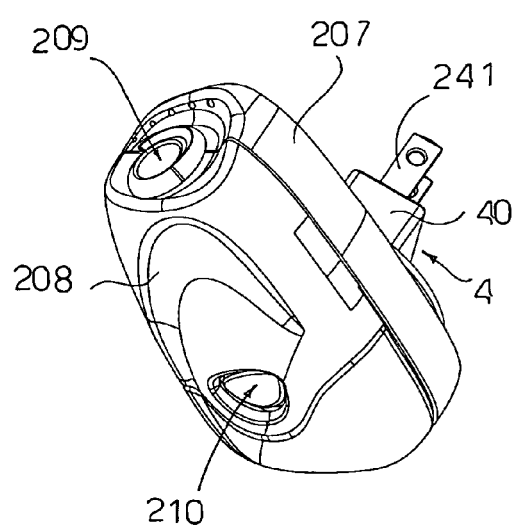
FIG. 11 is a perspective view showing an assembled diffusing device, which uses the plug and heating element assembly of FIG. 8.

As shown in FIG. 11, two outer shell halves 207, 208 are mounted on the assembly 200. The first shell half 207 is coupled rotatably to the flange 43 of the body of the plug 4 and the second shell half 208 is coupled to the heating element 2 and to the first shell half 207. The two half shells define a hole 209 designed to be disposed in register with a hole 221 which receives the wick. A hole 210 to favour the diffusion of the volatile substance is formed in the front surface of the shell half 208.

Assembly of the diffuser device is extremely simple and can be done automatically, precisely because the heating element is fixed integrally to the plug. After assembly of the outer shells 107 and 108, the weakened part 206 of the bridge 205 is cut with a tool so that the heating element is free from the plug and can therefore rotate with respect to the plug according to the arrangement of the electrical socket.

The body 20 of the heating element 2 is connected to the circular flange 43 of the plug 4 by means of a substantially L-shaped bridge 205. In this manner the axis of the tang 222 of the wick is maintained substantially parallel to the plane of the flange 43 of the plug.

The bridge 205 fixedly connects the heating element 20 to the plug 4. Thus the bridge 205 has reinforcing flanges 256 and 257 provided respectively on the front surface of the body 20 of the heating element and on the circular flange 43 of the plug. The elbow part of the bridge 205 has a weakening portion 206 having a reduced thickness so that it can be broken easily.

In FIGS. 8-10 a single bridge 205 has been illustrated; however, it is obvious that a plurality of bridges 205, distributed on the circular flange 43 of the plug and on the front surface of the body 20 of the heating element, can be foreseen.

Figure 12:
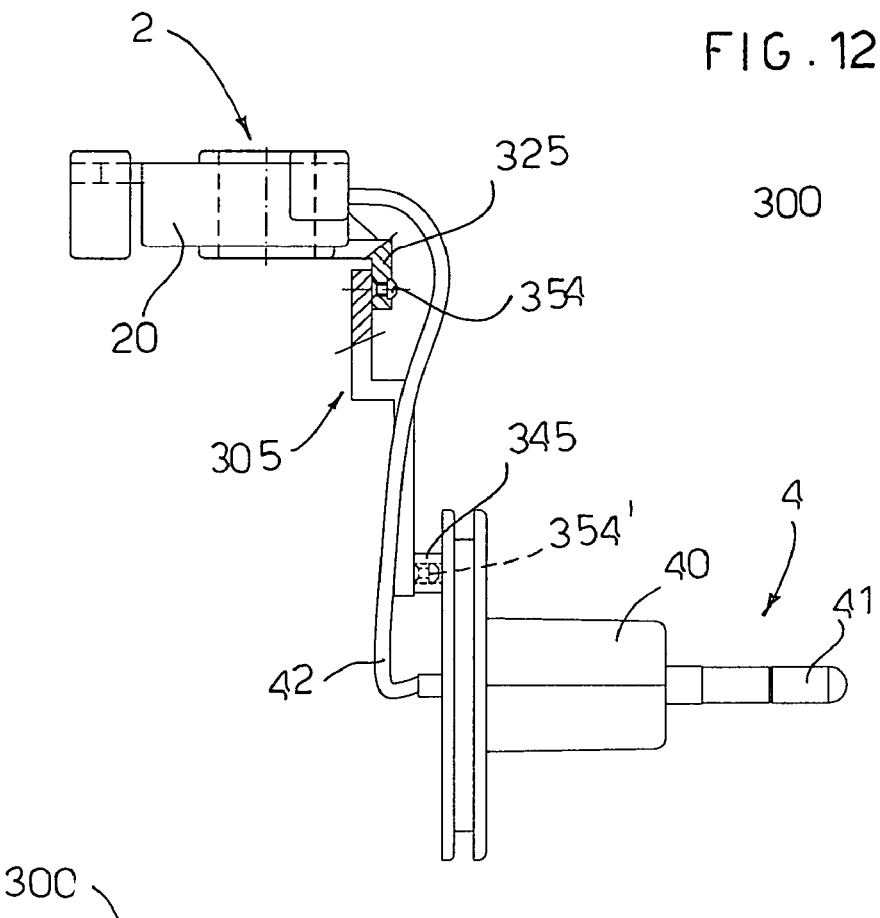
FIG. 12 is a side view showing a fourth embodiment of a plug and heating element assembly for a volatile substance diffusing device according to the invention.
Figure 13:
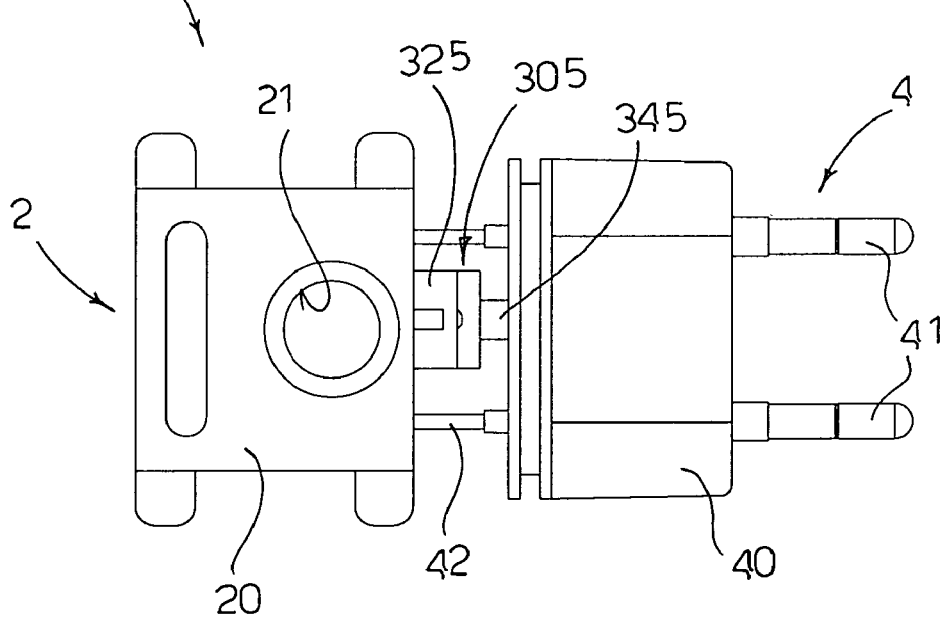
FIG. 13 is a top plan view of the plug and heating element assembly of FIG. 12.

In FIGS. 12 e 13 a plug and heating element assembly according to a fourth embodiment of the invention—indicated as a whole with reference numeral 300—is illustrated, in which the plug 4 and the heating element 2 are substantially the same as those illustrated in the first and in the second embodiments of the invention.

In this case the plug 4 and the heating element 2 are connected by a removable bridge 305. The bridge 305 has at it ends two pins 354 and 354' designed to engage, in a snap coupling relationship, in a protrusion 325 of the heating element and in a tang 345 disposed in the rear surface of the plug 4.

In this manner the bridge 305 keeps the heating element 2 and the plug 4 fixed in place during their movement and can be removed before the assembly thereof inside the shell of the diffuser, so as to be able to be reused or to be sent for disposal.

In the above described embodiments of the invention, the heating element and plug assembly can be disposed in plastic trays with special preformed seats. Thus mechanical arms, robots or gripping and placing arms are responsible for picking up the assembly and for placing it correctly inside the outer shell of the diffuser device. This operation is possible thanks to the fact that the heating element is connected to the plug.

Numerous changes and modifications of detail within the reach of a person skilled in the art can be made to the embodiments of the present invention without thereby departing from the scope of the invention as set forth in the appended claims.

The invention claimed is:

1. An assembly comprising a plug and a heating element for a diffuser device for volatile substances, wherein
   the plug comprises a body in which conducting poles for connection to an electrical socket are mounted, and
   the heating element comprises a body in which at least one electrical heating resistance connected by electrical wires to the poles of the plug is disposed and said body of the heating element is destined to be disposed near to or in contact with a support impregnated with volatile substances to be diffused,
   characterized in that the assembly further comprises
   at least one connector having a first end attached to said body of the plug and a second end attached to said body of the heating element, said connector configured with a breakable weakened part, so as to avoid relative movement of said body of the plug with respect to said body of the heating element until the weakened part is broken, which causes the body of the plug and the heating element to no longer be connected through the connector.

2. The assembly of claim 1, wherein the body of said plug has a rear circular flange able to engage rotatably with an outer shell of the diffusing device.

3. The assembly of claim 1, wherein said second end of said connector is integral with the body of the heating element.

4. The assembly of claim 1, wherein said first end of said connector is integral with the body of the plug and said second end of said connector is integral with the body of the heating element to prevent any relative movement of said heating element with respect to said plug.

5. The assembly of claim 4, wherein the connector is substantially L-shaped and the breakable weakened part is disposed at the elbow of the "L".

6. The assembly of claim 4, wherein the connector has ribs disposed in proximity to the heating element body and to the plug body.

7. An assembly comprising a plug and a heating element for a diffuser device for volatile substances, wherein:
   the plug comprises a body in which conducting poles for connection to an electrical socket are mounted;
   the heating element comprises a body in which at least one electrical heating resistance connected by electrical wires to the poles of the plug is disposed and the body of the heating element is destined to be disposed near to or in contact with a support impregnated with volatile substances to be diffused;
   at least one connector having a first end connected to the body of the plug and a second end connected to the body of the heating element, wherein the connector prevents relative movement of said body of the plug with respect to said body of the heating element; and
   the connector configured with a breakable weakened part so that, upon breaking the weakened part, the body of the plug is no longer connected to the body of the heating element by the connector and becomes moveable relative to the body of the heating element.

8. The assembly of claim 7, wherein the body of the plug has a rear circular flange configured to engage rotatably with an outer shell of the diffuser device when the weakened part becomes broken.

* * * * *